United States Patent [19]
Dubrul et al.

[11] Patent Number: 5,092,348
[45] Date of Patent: Mar. 3, 1992

[54] TEXTURED TISSUE EXPANDER

[75] Inventors: Will R. Dubrul, Santa Barbara, Calif.; G. Patrick Maxwell, Nashville, Tenn.

[73] Assignee: McGhan Medical Corporation, Santa Barbara, Calif.

[21] Appl. No.: 500,221

[22] Filed: Mar. 28, 1990

Related U.S. Application Data

[63] Continuation of Ser. No. 282,599, Jan. 17, 1989, abandoned.

[51] Int. Cl.$^5$ .................... A81B 19/00; A61M 5/32; A61F 2/12
[52] U.S. Cl. .................... 128/899; 606/192; 623/8
[58] Field of Search ............ 623/7, 8, 11, 12; 606/190, 191, 192; 128/899

[56] References Cited

U.S. PATENT DOCUMENTS

| | | | |
|---|---|---|---|
| 3,293,663 | 12/1966 | Cronin | 623/8 |
| 3,366,975 | 2/1968 | Pangman | 623/8 |
| 3,559,214 | 2/1971 | Pangman | 623/8 |
| 3,852,832 | 12/1974 | McGhan et al. | 623/8 |
| 4,648,880 | 3/1987 | Brauman | 623/8 |
| 4,666,447 | 5/1981 | Smith et al. | 623/8 |

OTHER PUBLICATIONS

Picha "Ion Beam Microtexturing of Biomat". MD & 01 Apr. 1984, pp. 39–42.
McGhaw, "Biocell Textured Mammary Implant" McGhaw Med. Corp. M057 10/87.
Pennis, "PU Covered Silicone Gel Mam . . . ", Aesthetic Plastic Surgery 9, 73 (1985) Ashlew, Further Studies . . . , Plastic & Reconstructive Surg. 42 (5), 421 (1970).
Brown et al., "Kinetics of Hydrolytic" NBS (Jul. 1979).
Sherman et al., "Biological Fate . . . ", J. Surg. Res. 9(3),167 (1969).
Picha et al., "Ion-Beam Microtexturing . . . ", MD and DI, 39 (1984).

*Primary Examiner*—David J. Isabella
*Attorney, Agent, or Firm*—Michael G. Petit

[57] ABSTRACT

An implantable tissue expansion device with an external surface layer of silicon elastomer, at least a portion of which contains a texture or open cell sturcture. The textured surface is expected to decrease subsequent capsular contracture and provide a non-skid surface to hold the device in position and permit differential expansion.

3 Claims, 1 Drawing Sheet

TEXTURED TISSUE EXPANDER

CROSS-REFERENCE TO RELATED APPLICATIONS

This is a continuation of application Ser. No. 07/282,599, filed Jan. 17, 1989, now abandoned.

FIELD OF THE INVENTION

The present invention is directed to tissue expansion devices suitable for either temporary implantation beneath the skin. More particularly, it is directed to silicone-elastomer tissue expanders having at least a portion of the outer surface of the shell textured.

BACKGROUND OF THE INVENTION

Skin and its subcutaneous tissue can greatly be expanded in area if the expansion is accomplished gradually. The extension of the skin over the pregnant female's abdomen is one example. Further, huge benign tumors often exist in various parts of the body, and the skin and subcutaneous tissue covering these tumors is greatly enlarged, but still is normal in color and texture.

A tissue expander is a device designed to be implanted beneath the skin then inflated to stretch the overlying skin and subcutaneous tissue. One use of tissue expanders is to generate an increased surface area of skin to be used for grafting or reconstruction. Another use is to slowly expand the overlying skin to create a pocket beneath the skin and subcutaneous tissue to receive a permanent prosthesis such as a mammary implant.

Silicone elastomers have long been used for the manufacture of implantable devices because they are chemically stable within the body as well as non-toxic. Notwithstanding the relative inertness of silicone elastomers, they may still provoke a foreign body reaction in some patients. When a foreign substance enters human tissue, the immediate and natural reaction of the tissues surrounding the foreign substance is to render it harmless to the rest of the body. A large, inert foreign body is encapsulated in a sheath of fibrous tissue to isolate it from surrounding tissues. Encapsulation is a defensive mechanism that occurs through a process similar to the formation of scar tissue in the healing of a wound or surgical incision. A fibrous tissue capsule will form around and completely enclose an implanted device such as a tissue expander or permanent prosthesis in an intimate fashion, conforming to the respective shapes and curvatures of the device.

Capsule formation is not a problem for the patient unless the capsule begins to contract. Contracture of the capsule around an implant causes the implant to be compressed tightly and feel very hard and rigid. Ultimately, the contracted capsule may assume a nearly spherical shape causing discomfort and constitutes a serious medical problem.

One way to remedy capsular contracture is to surgically remove the contracted capsule and implant and then insert either the same or another implant, a procedure called surgical capsulotomy or capsulectomy. Alternatively, some doctors use closed capsulotomy, a method wherein force is applied to break the capsule in situ. Of course, capsular contracture can still recur.

The genesis of capsular contracture is complex and the reasons why it occurs are not yet fully understood. Nonetheless, several different approaches to avoiding capsular contraction have been investigated. One of the most popular approaches involves the use of steroids. Steroids are known to possess anti-inflammatory and anti-fibrinogenic properties. However, the use of steroids can result in complications such as tissue atrophy and discoloration of the skin. Accordingly, controversy surrounds the use of steroids and their relative utility in preventing capsular contracture. Other drugs and techniques have also been suggested, but their utility has not yet been established.

Other approaches to the problem of capsular contracture have focused on the design of the implant. One such device (U.S. Pat. Nos. 3,366,975 and 3,559,214) is described as a permanent prosthesis made of a flexible, thin-walled container or sac composed of a material impervious to the ingrowth of fibrous tissue, such as a silicone elastomer, to the external surface of which a thin layer of a porous or open-celled material has been adheringly applied. The interior of the sac is filled with an inert material approximating the resiliency of normal mammary tissue, such as a saline solution or a silicone gel.

The porous or open-celled layer is normally composed of a polyether, polyester or polyurethane foam material. Thin layers of this type of material have been applied to the back sides of mammary prostheses so that fibrous tissue could grow into the material and thereby anchor a prosthesis securely to the chest wall (U.S. Pat. No. 3,293,663). However, case studies conducted on mammary prostheses almost completely covered with a thin foam layer indicated that the incidence of capsular contracture was reduced by the use of such prostheses (Pennisi, *Polyurethane-Covered Silicone Gel Mammary Prosthesis for Successful Breast Reconstruction*, Aesthetic Plastic Surgery, Vol. 9 at 73 (1985); Ashley, *Further Studies on the Natural-Y Breast Prosthesis*, Plastic and Reconstructive Surgery, Vol. 45, No. 5 at 421 (May 1970)). Although the cause for the reduced incidence is not fully understood, it is believed that the growth of the fibrous tissue into the open-cell layer from many directions prevents the fibrous tissue from contracting in a concerted manner. In other words, the contractions occur in many directions and tend to neutralize each other (Pennisi, supra, at 73).

However, possible problems exist with the use of polyether, polyester or polyurethane foam materials in implants. These materials apparently degrade in the body over a period of time (Brown, Lowry and Smith, *The Kinetics of Hydrolytic Aging of Polyester Urethane Elastomers*, National Bureau of Standards (July 1979); Sherman and Lyons, *The Biological Fate of Implanted Rigid Polyurethane Foam*, Journal of Surgical Research, Vol. 9, No. 3 at 167 (March 1969)). Therefore, the effectiveness of these materials for preventing capsular contracture may disappear as they degrade. These materials have also been suspected of creating problems with infection and of being carcinogenic.

To avoid the potential problems with existing foam materials and still take advantage of the reduced incidence of capsular contracture attendant with the use of prostheses having a porous or open-celled outer layer, ways have been sought to make a layer of silicone elastomer having an open-cell texture. In U.S. Pat. No. 3,852,832, a mammary prosthesis is disclosed having a fixation means attached to its back side with perforations passing therethrough and ribs projecting therefrom. This fixation means is preferably to be made of a silicone elastomer. Although no method for making such a fixation means is disclosed, it is believed that it would be separately molded. Therefore, the pattern of perforations and ribs would have to be such as to allow removal from a mold. The fixation means must then be attached to the prosthesis.

Surprisingly, tissue expanders designed for temporary implantation have not been textured. We say "surprisingly" because although a tissue expander is a temporary implant, the surface that it presents to the surrounding tissue will set the stage for capsule genesis. Tissue expanders are used to create a pocket beneath the skin of the desired size and shape to accommodate a permanently implantable prosthesis. For example Brauman (U.S. Pat. No. 4,648,880) teaches a method of texturing the surface of an implantable prosthetic device using a dacron laminate as an outer cover. A tissue expander, however, is not a prosthetic device. It is a temporarily implantable tool used to create a pocket for an implantable prosthesis. Fibroblasts, migrating to the surface of a tissue expander, will secrete fibrin. The fibrin molecules will orient themselves to encase the implant. If the surface is "rough", that is, the surface has pits or irregularities that are on the order of 10 or 20 molecular dimensions, the fibrin molecules will follow the contour of the roughened surface structure when the capsule is in its embryonic stage of development. The template thus formed will serve as a support for further deposition of fibrin, which in turn, will form a dimpled sheath around the implant. If the diameter of the pit in the surface of the device is too small, the fibril molecules will not follow the contour change during deposition. If the pits in the surface are too deep, therefor ingrowth of fibroplasts or filaments of fibrin would make it difficult to remove the expander without destroying the embryonic capsule that has been so carefully prepared to prevent subsequent contracture when the permanent prosthetic device is implanted. Accordingly, a need exists for a silicone elastomer tissue expander device having a textured, preferably open-celled, surface therefor, which will disperse or disorganize the force of encapsulating tissue to minimize formation of a spherical capsular contracture. Another object of the present invention is to provide a tissue expander which can readily be removed in its entirety, if desired, from the human body without encountering any untoward affects.

SUMMARY OF THE INVENTION

Smooth wall tissue expanders have been found to have many clinical problems which contribute to complications or limit their effectiveness. Slavin and Colen have documented an unacceptably high complication rate in breast reconstruction with smooth wall tissue expanders due to extrusion, migration, malfunction of the port valve, infection, and product failure (presented at the Annual Meeting of the American Assoc. Plast. Surgeons, May 10, 1989, Scottsdale, Ariz.). Armstrong et al have also found that breast reconstruction with smooth wall tissue expanders has an unacceptable infection rate (24%, (Ann. Plast. Surg. 23:284, 1989). Ramirez and Orlando found that smooth wall tissue expanders used in breast reconstruction caused considerable pain on expansion as well as deformity of the body chest thorax (Plast. Surg. Form 9:148, 1986). Pain has been such a problem following inflation of the smooth wall expanders that Cohen et al and Berman et al have studied injection of lidocaine into the expander at the time of its fill in an effort to minimize the pain (Plast. Reconstr. Surg. 79:489, 1983; Clin. Plast. Surg. 14:491, 1987; Plast. Reconstr. Surg. 84:621, 1989). Sinow et al (Plast. Surg. Forum 12:174, 1989) have also studied the chest wall deformity problem during expansion in a prospective longitudinal study. They measured clinically the pre- and post-expansion intraluminal pressures within smooth wall tissue expanders implanted in female chests and found a high degree of correlation between high intraluminal pressure and pain.

Other clinical problems with smooth wall tissue expanders seen in breast reconstruction consist of displacement of the tissue expander due to migration of the expander with capsule contracture (Plast. Surg. Forum 12:145, 1989), lack of ability to obtain an adequate expansion volume due to capsular contracture around the expander (Plast. Surg. Forum 12:146, 1989) and the necessity of removing the thickened capsule contracture formed around the expander at the time of the second operation where the permanent prosthesis is placed (Plast. Surg. Form 12:146, 1989). Other problems with smooth wall tissue expanders found in breast reconstruction have been the inability to accurately form an inframammary fold via expansion necessitating surgical inframammary fold creation at the time of the second operation by internal or external means (Plast. Reconstr. Surg. 8:387, 1987; Plast. Reconstr. Surg. 60:523, 1977). To overcome the foregoing problems associated with the smooth wall expander, we conceived the idea of a textured surfaced silicone expander.

In the most general terms, the present invention is directed to a tissue expander device for temporary implantation beneath the skin comprised of silicone elastomer and having an outer layer, or shell, at least a portion of which has a textured, preferably open-cell structure at the surface.

More specifically, the present invention is directed to an improved silicone-elastomer shell for a tissue expansion device, the improvement comprising: at least a portion of the external surface of the tissue expander device having textured preferably open-cell structure.

One objective of the invention is to provide a tissue expander that will stay where it is placed.

Another object of the invention is to provide a tissue expander device which will minimize capsular contracture around the tissue expander.

Still another object of the invention is to prevent or minimize capsular contracture associated with implantation of a permanent prosthesis into the site created by the tissue expander device.

These and other objects of the invention will be better understood by turning now to the preferred embodiments.

DETAILED DESCRIPTION OF THE PREFERRED EMBODIMENT

The preferred embodiment of the present invention will primarily be described in the context of a mammary tissue expander because the present invention is expected to help solve the capsular contraction problem that is particularly troublesome in the implantation of mammary prostheses. However, the present invention should not be considered as applicable to such a prosthesis. Instead, the teachings of the present invention should prove to be advantageous wherever a tissue expander is used to create a pocket for such a permanent prosthesis, even if the prosthesis is not textured and where capsular contraction can damage a medical implant or cause discomfort to the patient. In summary, the present invention should have general application within the field of reconstructive surgery, as it can be used to create a pocket for any of a wide variety of prostheses.

Figure 1:
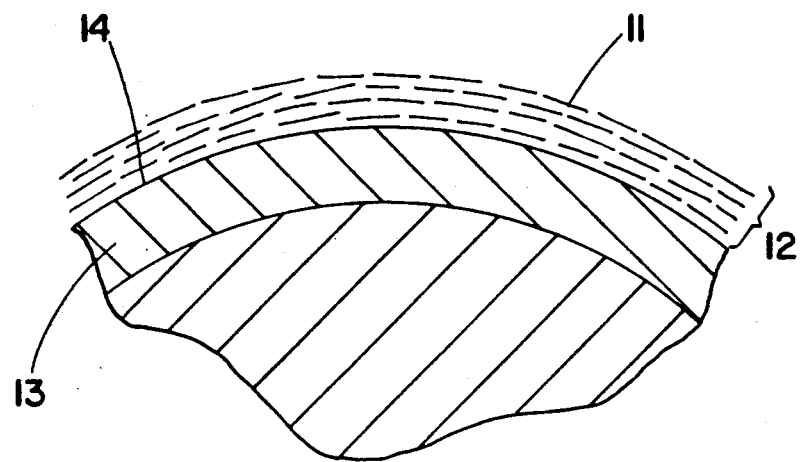
FIG. 1 is a magnified sectioned side view of the external surface of the shell of a conventional prior art tissue expansion device showing no open-cell structure and the orientation of fibrin molecules in the capsule surrounding the expander.

FIG. 1 shows the orientation of fibrin molecules (11) comprising the capsule (12) surrounding the shell (13) of a tissue expander device with a smooth surface (14) as taught by the prior art. It is to be expected that the high degree of orientation exhibited by the fibrin molecules during the early stages of capsule genesis will persist, layer upon layer like an onion, even after the smooth surfaced prior art expander has been removed and replaced with a textured permanent implant as taught, for example, by Braumen.

Figure 2:
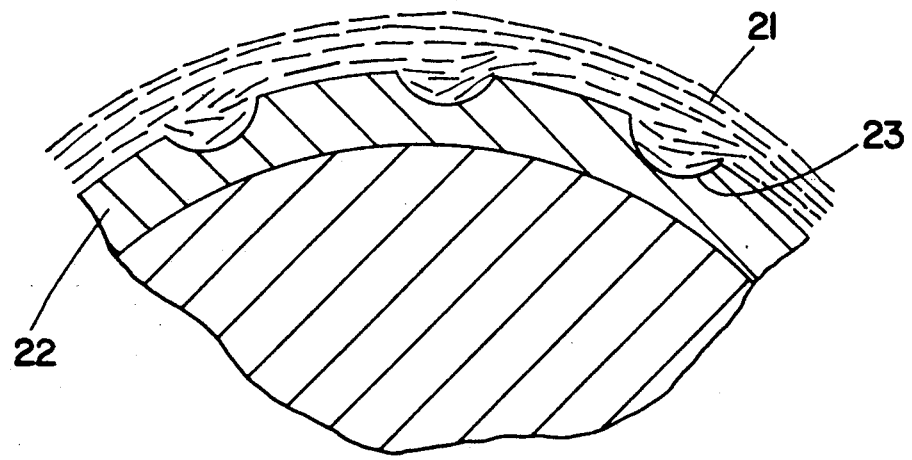
FIG. 2 is a magnified sectioned side view of the external surface of the shell of a tissue expander of the current invention showing the open-cell structure and the orientation of the capsular fibrin molecules with respect to the surface of the shell.

FIG. 2 shows the general organization of capsular fibrin molecules (21) contiguous with the surface of a tissue expander shell (22) containing a random pattern of open cells (23). upon the surface of a tissue expander device.

The method used to form the open-cell structure is chosen to create a random, interconnected bubble structure. The cells preferably have diameters ranging from about 10 to about 600 microns and a depth ranging from a portion of one cell diameter to a multiple of many cell diameters.

Ion-beam thruster technology has been suggested as a way to microtexture breast prostheses (Picha and Siedlak, Ion-Beam Microtexturing of Biomaterials, MD & DI at 39 (April 1984)).

Another method and the method of choice in making the preferred embodiment, comprises the steps of: applying solid particles to the surface before the layer is fully cured; fully curing the layer; and dissolving the solid particles with a solvent that does not dissolve the silicone elastomer to any appreciable extent. A tissue expander device made by this method is expected to have great utility in preventing capsular contraction and in anchoring the tissue expander firmly in place during the expansion process which may take several weeks.

EXAMPLE 1

We initiated laboratory studies in New Zealand white rabbits comparing smooth wall tissue expanders with textured surface silicone tissue expanders. Polyurethane-covered expanders were also compared in this research model (Plast. Surg. Forum 12:70, 1989). The compliance or lack of stiffness (and thus expandability) of the surrounding capsule were analyzed by conversion to modulus and evaluation of energy absorption. The modulus may be thought of as a measure of capsular brittleness. The lower the modulus, the more expandable the capsule. The higher the total absorbed energy, the less brittle, therefore, the more expandable the surrounding capsule. These studies have demonstrated that the textured silicone expander has a lower modular than a smooth wall tissue expander. There is also statistically significant evidence of a higher energy absorption with a textured surface tissue expander than with the smooth wall expander). In this (rabbit) laboratory model, the silicone textured surface tissue expander has a more expandable capsule demonstrating reduced capsular contracture and is therefore an improvement over a smooth silicone surface.

EXAMPLE 2

We have also evaluated 54 patients with 77 textured silicone expanders clinically implanted over a two-year period. The clinical results have all been superior to clinical results with smooth wall expanders (Plast. Surg. Forum 12:146, 1989) for the following reasons:

1. The immobile textured expanders stay where they are initially placed.
2. Expansion is easier due to less patient discomfort and minimal capsule contracture formation around the expander.
3. Infection has been less due to tissue adherence of the textured surface of the integral injection site. (With smooth wall expanders there is a periprosthetic space usually containing a small amount of fluid.)
4. The inframammary fold forms accurately during the expansion process, facilitated by tissue adherence and the lack of displacement of the expander.
5. On expander removal the permanent implant can be placed in the expanded pocket without the need for capsule removal.

Our clinical results support the textured prostheses as being softer than the smooth wall implant. This appears to be especially true when comparing the two devices long-term.

I have independently and solely originated the idea of a textured silicone expander. I have confirmed its effectiveness clinically. The foregoing specification documents the problems that exist with current smooth-walled tissue expanders, and how those problems have been solved with the textured silicone expander.

The foregoing description of the preferred embodiment of this invention is presented for the sole purpose of instruction. The scope of the invention can best be understood by turning now to the claims.

What is claimed is:

1. An improved tissue expansion device for temporary surgical implantation beneath the skin and for removal upon predetermined expansion of the overlying tissue, the device comprising an expandable biocompatible envelope forming an expandable fluid-tight chamber, an injection reservoir in fluid communication with the chamber, the injection reservoir comprising means for injecting fluid into the chamber from a hypodermic needle which punctures the injection reservoir, and said envelope having a textured outer surface over at least a portion of said envelope.

2. The improvement of claim 1 wherein the textured surface is of an open-celled configuration.

3. A tissue expander for temporary implantation, comprising an expandable outer shell enclosing an expandable lumen for temporary implantation beneath the skin thereafter to be inflated to stretch and expand the overlying tissue, and at least a portion of the outer surface of said shell being textured.

* * * * *